(12) United States Patent
Ash

(10) Patent No.: US 6,409,699 B1
(45) Date of Patent: Jun. 25, 2002

(54) CONTINUOUS FLOW-THROUGH PERITONEAL DIALYSIS (CFPD) METHOD WITH CONTROL OF INTRAPERITONEAL PRESSURE

(75) Inventor: Stephen R. Ash, Lafayette, IN (US)

(73) Assignee: Renal Solutions, Inc., West Lafayette, IN (US)

( * ) Notice: Subject to any disclaimer, the term of this patent is extended or adjusted under 35 U.S.C. 154(b) by 0 days.

(21) Appl. No.: 09/284,904

(22) PCT Filed: Oct. 22, 1997

(86) PCT No.: PCT/US97/19489

§ 371 (c)(1),
(2), (4) Date: Jun. 28, 1999

(87) PCT Pub. No.: WO98/17333

PCT Pub. Date: Apr. 30, 1998

Related U.S. Application Data

(60) Provisional application No. 60/029,062, filed on Oct. 22, 1996.

(51) Int. Cl.[7] .............................................. A61M 1/00
(52) U.S. Cl. ....................................................... 604/29
(58) Field of Search ......................... 604/29; 435/289.1, 435/299.1

(56) References Cited

U.S. PATENT DOCUMENTS

| | | |
|---|---|---|
| 3,707,967 A | 1/1973 | Kitrilakis et al. |
| 4,338,190 A | 7/1982 | Kraus et al. ................. 210/195 |
| 4,586,920 A | 5/1986 | Peabody .................... 604/29 |
| 4,705,628 A | 11/1987 | Yamamoto et al. ......... 210/289 |
| 4,718,890 A | 1/1988 | Peabody ........................ 604/29 |
| 4,747,822 A | 5/1988 | Peabody ........................ 604/29 |
| 4,854,322 A | 8/1989 | Ash et al. .................... 128/635 |
| 4,950,259 A | 8/1990 | Geary et al. |
| 5,141,493 A | 8/1992 | Jacobsen et al. .............. 604/29 |
| 5,261,876 A | 11/1993 | Popovich et al. ............. 604/28 |
| 5,270,192 A | 12/1993 | Li et al. ..................... 435/174 |
| 5,277,820 A | 1/1994 | Ash ........................... 210/646 |
| 5,322,519 A | 6/1994 | Ash ........................... 604/264 |
| 5,338,293 A | 8/1994 | Jeppsson et al. .............. 604/29 |
| 5,368,555 A | 11/1994 | Sussman et al. ............... 604/4 |
| 5,605,835 A | 2/1997 | Hu et al. .................... 435/297 |
| 6,030,358 A | * 2/2000 | Odland |

FOREIGN PATENT DOCUMENTS

| | | |
|---|---|---|
| DE | 21 49 040 | 4/1972 |
| EP | 0 498 382 | 8/1992 |

OTHER PUBLICATIONS

Ash, Stephen R., Janle, Elsa M., Continuous flow–through peritoneal dialysis (CFPD): Comparison of efficiency to IPD, TPD and CAPD in an animal model, Peritoneal Dialysis International, vol. 17, No. 4, pp. 365–372, © 1997 International Society for Peritoneal Dialysis.

(List continued on next page.)

Primary Examiner—Mark Bockelman
(74) Attorney, Agent, or Firm—Woodward, Emhardt, Naughton Moriarty & McNett; Patent and Trademark Attorneys

(57) ABSTRACT

The present invention relates generally to advantageous devices and methods for treating patients suffering from renal insufficiency and/or hepatic insufficiency. More particularly, the invention relates in certain aspects to devices and methods for performing continuous flow-through peritoneal dialysis (CFPD). In other aspects of the invention, peritoneal dialysis systems are provided which utilizes a bioreactor to regenerate peritoneal fluid for re-infusion into a peritoneal cavity. The invention, therefore, provides advantageous systems for passing fluid through a patient's peritoneal cavity at a relatively high flow rate, while maintaining in the peritoneal cavity an optimal dialysate pressure, to thereby alter the contents of the patient's blood by diffusion of molecules through the peritoneal membrane.

41 Claims, 7 Drawing Sheets

OTHER PUBLICATIONS

Gordon, A.; Lewin, A.J.; Maxwell, M.H.; Morales, N.D., Augmentation of Efficiency by Continuous Flow Sorbent Regenration Peritoneal Dialysis, Trans. Amer. Soc. Artif. Int. Organs, vol. XXII, pp. 599–603, 1976.

Shinaberger, James H.; Shear, Leroy; Barrye, Kevin G., Increasing Efficiency of Peritoneal Dialysis Experience with Pertoneal–Extracorporeal Recirculation Dialysis, Trans. Amer. Soc. Artif. Int. Organs, vol. XI, pp. 76–82, 1965.

Lewin, A.J.; Greenbaum, M.A.; Gordon, A.; Maxwell, M.H., Sorbent Based Regenerating Delivery System for Use in Peritoneal Dialysis, Trans. Amer. Soc. Artif. Int. Organs, Vox. XX, pp. 130–133, 1974.

Lange, Kurt; Treser, Gerhard, Automatic Continuous High Flow Rate Peritoneal Dialysis, Trans. Amer. Soc. Artif. Int. Organs, vol. XIII, pp. 164–167, 1967.

Galletti, Pierre M.; Jauregui, Hugo O., *Liver Support Systems*, Chp. 129, pp. 1952–1966, © 1995 by CRC Press.

Lysaght, Michael J.; Moran, John, *Peritoneal Dialysis Equipment,* Chp. 127, pp. 1923–1935, © 1995 by CRC Press.

Galletti, Pierre M.; Colton, Clark K.; Lysaght, Michael J., *Artificial Kidney,* Chp. 126, pp. 1898–1922, © 1995 by CRC Press.

Abstract submitted in Oct., 1996; accepted for the $17^{th}$ Annual Conference on Peritoneal Dialysis; presented at the conference on Feb. 16–18, 1997; and published as follows: Ash, S.R., Janle, E.M., Continuous flow–through peritoneal dialysis (CFPD): comparison of efficiency to IPD, TPD, and CPAD in an animal model, Peritoneal Dialysis International 17(1): 55, 1997.

Raja, Rasib M., Kramer, Mark S., and Rosenbaum, Jerry L., Recirculation Peritoneal Dialysis with Sorbent Redy Cartridge, Nephron, vol. 16, pp. 134–142; © 1976.

* cited by examiner

CONTINUOUS FLOW-THROUGH PERITONEAL DIALYSIS (CFPD) METHOD WITH CONTROL OF INTRAPERITONEAL PRESSURE

REFERENCE TO RELATED APPLICATIONS

This application is a 371 of PCT/US97/19489 which claims the benefit of U.S. Provisional Application No. 60/029,062, filed Oct. 22, 1996, which is incorporated by reference herein in its entirety.

BACKGROUND OF THE INVENTION

1. Field of the Invention

The present invention relates generally to devices and methods for treating patients suffering from renal insufficiency and/or hepatic insufficiency. More particularly, the invention relates to devices and methods for performing continuous flow-through peritoneal dialysis.

2. Discussion of Related Technology

Irreversible end-stage kidney disease was recently reported to occur with an annual frequency of about 1 in 5000 to 10,000 in the general population, with this rate increasing. Until the 1960s, such disease was universally fatal. In the last four decades, various interventions have been developed and implemented for preserving life after loss of all or most of a patient's own kidney function.

The normal function of the mammalian kidney includes such activity as maintaining a constant acid-base and electrolyte balance, removing excess fluids and removing undesirable products of the body's metabolism from the blood. In an individual with end stage renal disease, this functioning of the kidney may be reduced to as low as 5% or less of the normal level. When renal function has decreased to this point, artificial means must then be employed to substitute for the kidney activity, if life is to be sustained. This is accomplished clinically by the use of dialysis.

One of the most common methods for achieving this is hemodialysis, in which the patient's blood is moved outside of the patient's body and passed through an artificial kidney dialysis machine. In the machine, a synthetic non-permeable membrane acts as an artificial kidney with which the patient's blood is contacted on one side; on the opposite side of the membrane is a dialyzing fluid or dialysate, the composition of which is such that the undesirable products in the patient's blood will naturally pass across the membrane by diffusion, into the fluid. The blood is thus cleansed, in essentially the same manner as the kidney would have done, and the blood is returned to the patient's body.

There are, however, a number of disadvantages inherently associated with hemodialysis. For instance, poor peripheral vasculature in some patients makes removal of the patient's blood for hemodialysis unfeasable. Additionally, extracorporeal handling of blood is inherently dangerous due to the risk of introducing, for example, bacterial or other contaminants or air bubbles into the blood. Further, equipment needed for performing hemodialysis is guide complicated and expensive.

Some of the disadvantages associated with extracorporeal treatment of blood by hemodialysis are overcome by the use of techniques which utilize the patient's own peritoneum as the required semipermeable membrane. Presently, a great deal of interest is being given to the development of improved methods for removing undesirable products from the blood through the peritoneum, an intricate membrane-like tissue that lines the abdominal cavity and covers the liver, kidneys, intestine and other internal organs. The peritoneum contains large numbers of blood vessels and capillaries and is thus capable of acting as a natural semipermeable membrane. In a peritoneal dialysis procedure, dialysis solution, or "dialysate" is introduced into the peritoneal cavity, via a catheter in the abdominal wall, and a suitable period of residence time for the dialysate is typically allowed to permit the exchange of solutes between it and the blood. The waste products removed from the patient's blood in this manner typically consist of solutes like sodium and chloride ions, and the other compounds normally excreted through the kidneys like urea, creatinine, and water. Fluid removal is achieved by providing a suitable osmotic gradient from the blood to the dialysate to permit water outflow from the blood. The diffusion of water across the peritoneal membrane during dialysis is called ultrafiltration. Conventional peritoneal dialysis solutions include glucose in concentrations sufficient to generate the necessary osmotic pressure to remove water from the patient's blood. Thus, the proper acid-base, electrolyte and fluid balance is returned to the blood and the dialysis solution is simply drained from the body cavity through the catheter.

Continuous Ambulatory Peritoneal Dialysis (CAPD) is a popular form of peritoneal dialysis (PD). A patient performs CAPD manually about four times a day. During CAPD, the patient drains spent peritoneal dialysis solution from his/her peritoneal cavity. The patient then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours. The APD sequence typically lasts for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle.

During the fill phase, the cycler transfers a predetermined volume of fresh, warmed dialysate into the peritoneal cavity of the patient. The dialysate remains (or "dwells") within the peritoneal cavity for a time. This is called the dwell phase. During the drain phase, the cycler removes the spent dialysate from the peritoneal cavity. The number of fill/dwell/drain cycles that are required during a given APD session depends upon the total volume of dialysate prescribed for the patient's APD regime.

Continuous Cycling Peritoneal Dialysis (CCPD) is one commonly-used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 6 fill/dwell/drain cycles to achieve a prescribed therapy volume. After the last prescribed fill/dwell/drain cycle in CCPD, the cycler infuses a final fill volume. The final fill volume dwells in the patient through the day. It is drained at the outset of the next CCPD session in the evening. The final fill volume can contain a different concentration of glucose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home. Like CCPD, IPD involves a series of fill/dwell/drain cycles. The cycles in IPD are typically closer in time than in CCPD. In addition, unlike CCPD, IPD does not include a final fill phase. In IPD, the patient's peritoneal cavity is left free of dialysate (or "dry") in between APD therapy sessions.

Tidal Peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse then drain a replacement volume on top of the base volume, except for the last drain phase. The last drain phase removes all dialysate from the peritoneal cavity. There is a variation of TPD that includes cycles during which the patient is completely drained and infused with a new fill base volume of dialysis. TPD can include a final fill cycle, like CCPD. Alternatively, TPD can avoid the final fill cycle, like IPD.

While there are a number of peritoneal dialysis techniques available which generally provide a less-intrusive and safer alternative to extracorporeal hemodialysis, methods have not hereinbefore been provided which achieve optimal clearance of toxins from the blood. In an attempt to overcome this problem, an alternative type of PD has been explored, called Continuous Flow-through Peritoneal dialysis (CFPD). A few studies in the past have shown that higher efficiency of chemical transfer in PD can be achieved if fluid is directed through the peritoneum in a unidirectional manner, from the right to left side of the peritoneum. Gordon A, Lewin A J, Maxwell M H, Morales N D. Augmentation of efficiency by continuous flow sorbent regeneration peritoneal dialysis. *Trans ASAIO* 23: 599–604, 1976; Shinaberger J M, Shear L, Barry K G. Increasing efficiency of peritoneal dialysis. Experience with peritoneal-extracorporeal recirculation dialysis. *Trans ASAIO* 11: 76, 1965; and Raja R M, Kramer M S, Rosenbaum J L. Recirculation peritoneal dialysis with sorbent REDY cartridge. *Trans ASAIO* 13:164, 1967. For Example, with 100 ml/min of dialysate flow, creatinine clearances of up to 20 ml/min have been achieved, many times the clearances of CAPD. However, there were disadvantages associated with this type of therapy, and it did not gain acceptance as a suitable alternative to other PD techniques. One disadvantage was that this procedure required two catheters rather than one. Additionally, difficulty has been experienced in achieving continuous outflow at sufficient rates without experiencing blockage of the outflow catheter. As such, there is a need in the art for improved devices and methods for performing CFPD.

Turning now to an additional need for blood purification techniques, the liver is another organ which functions to purify blood. Additionally, the liver performs many additional complex biological functions that are critical for the homeostasis of the human body. Although individual pathways for synthesis and breakdown of carbohydrates, lipids, amino acids, proteins, and nucleic acids can be identified in other mammalian cells, only the liver performs all these biochemical transformations simultaneously and is able to combine them to accomplish its vital biologic task. The liver is also the principal site of biotransformation, activation or inactivation of drugs and synthetic chemicals. Therefore, this organ displays a unique biologic complexity. When it fails, functional replacement presents one of the most difficult challenges in substitutive medicine. Artificial means, such as those used to substitute for kidney activity, are not as direct when replacement of liver function is needed.

Under normal physiologic requirements, the liver modifies the composition and concentration of the incoming nutrients for its own usage and for the benefit of other tissues. Among the major liver functions, the detoxification of foreign toxic substances (xenobiotics), the regulation of essential nutrients, and the secretion of transport proteins and critical plasma components of the blood coagulation system are probably the main elements to evaluate in a successful organ replacement. The liver also synthesizes several other critical proteins, excretes bile, and stores excess products for later usage, functions that can temporarily be dispensed with but must eventually be provided. The challenge of liver support in case of organ failure is apparent from the complexity of functions served by liver cells and from our still imperfect ability to rank these functions in terms of urgency of replacement.

The concept of artificial liver support is predicated on the therapeutic benefit for removing toxic substances accumulating in the circulation of liver failure patients. Technologies for temporary liver support focus on the detoxifying function, since this appears to be the most urgent problem in liver failure. The procedures and devices which have been considered for this purpose include the following:

Hemodialysis

Hemodialysis with conventional cellulosic membranes (cut-off point around 5000 daltons) or more permeable polysulfone or polyacrylonitrile (cut-off around 30,000 daltons) helps to restore electrolyte and acid-base balance and may decrease the blood ammonia levels but cannot remove large molecules and plasma protein-bound toxins. Improvement of the patient's clinical condition (e.g., amelioration of consciousness and cerebral edema) is temporary. The treatment appears to have no lasting value and no demonstrated effect on patient survival. In addition, hemodialysis may produce a respiratory distress syndrome caused by a complement-mediated poly-morphonuclear cell aggregation in the pulmonary circulatory bed. Because some of the clinical benefit seems related to the removal of toxic molecules, more aggressive approaches focused on detoxification have been attempted.

Hemofiltration

Hemofiltration with high cut-off point membranes (around 50,000 daltons with some poly-acrylonitrile-polyvinyl chloride copolymers, modified cellulose's, or polysulfones) clears natural or abnormal compounds within limits imposed by convective transport across the exchange membrane. These procedures again have a temporary favorable effect on hepatic encephalopathy (perhaps because of the correction of toxic levels of certain amino acids) with reversal of coma, but they do not clearly improve survival rates.

Hemoperfusion

Hemoperfusion, i.e., extracorporeal circulation of blood over nonspecific sorbents (e.g., activated charcoal) or more complex biochemical reactors which allow the chemical processing of specific biologic products, such as ammonia, have not yet met clinical success in spite of encouraging experimental results, except in the case of hepatic necrosis induced by poisonous mushrooms such as Amanita phalloides. Anion exchange resins and affinity columns similar to those used in separative chromatography may help in removing protein-bound substances (e.g., bilirubin) which would not pass through hemodialysis or hemofiltration membranes, but nonspecific sorbents may also deplete the plasma of biologically important substances. Further, these techniques are complicated by problems of hemocompatibility, related in part to the entertainment of dust ("fines") associated with the sorbent material itself and in part to platelet activation in patients with an already compromised coagulation status. To minimize this problem, direct blood or plasma contact with the sorbent material can be avoided by polymer coating of the sorbent particles using either albumin, cellulose nitrate, or similar thin films, but hemocompatability remains a concern. Here again, there is anecdotal evidence of clinical improvement of hepatic failure with hemoperfusion, with some reports claiming a higher survival rate in hepatic encephalopathy, but these reports have not been supported by well-controlled studies. As is the case for hemodialysis and hemofiltration, the possible beneficial effect of hemoperfusion should be evaluated in the context of the clinical variability in the course of fulminant hepatic failure.

Plasmapheresis

Plasmapheresis, i.e., the combination of withdrawal of blood, centrifigation, or membrane processing to separate and discard the patient's plasma, and return of autologous cells diluted with donor plasma, was practiced initially as a batch process. Techniques now exist for a continuous exchange process, in which plasma and cells are separated by physical means outside of the body (membrane separation or centrifugation), and the patient's plasma replaced by banked plasma (up to 5000 ml per day). There is evidence from controlled clinical trials for the effectiveness of this form of therapy, but the mortality rate remains high in patients with hepatic failure, whether from insufficient treatment or the risks of the procedure. It appears, however, that plasma exchange can be beneficial in the preoperative period prior to liver transplantation so as to correct severe coagulopathy. Plasmapheresis is used in conjunction with the placement of a hepatocyte-seeded extracorporeal hollow-fiber device to treat acute and chronic liver.

Combined Therapy

Endotoxins and cytokines can be removed by hemoperfusion over activated charcoal and adsorbent resins, but it may be more effective to process plasma than whole blood. This has led to the concept of combining plasmapheresis with continuous plasma treatment for removal of substances such as tumor necrosis factor (TNF), interleukin-6 (IL-6), and bile acids by a resin column, and then ultrafiltration or dialysis for fluid removal, since patients with liver failure often develop secondary renal failure.

Hemoperfusion Over Liver Tissue Slices

The incorporation of active hepatocytes in a hemoperfusion circuit was suggested by the laboratory practice of biochemists who have investigated metabolic pathways in tissue slices. For liver replacement, this technology has been pursued primarily in Japan as a substitute for organ transplantation, which is culturally frowned upon in that country, in spite of a major incidence of severe liver disease. The procedure may improve biochemical markers of liver failure but has, to date, failed to demonstrated clinical value.

In view of the insufficiency of the above treatments to satisfactorily treat a patient suffering from hepatic insufficiency, there is a great need in the art for improved devices and methods for treating such a patient. Such devices and methods are provided by the present invention, in which there are provided peritoneal dialysis devices and methods which improve the blood composition of a patient suffering from hepatic insufficiency.

SUMMARY OF THE INVENTION

The present invention relates generally to advantageous devices and methods for treating patients suffering from renal insufficiency and/or hepatic insufficiency. More particularly, the invention relates in certain aspects to devices and methods for performing continuous flow-through peritoneal dialysis (CFPD). In another aspect of the invention, a peritoneal dialysis system is provided which utilizes a bioreactor to regenerate peritoneal fluid for re-infusion into a peritoneal cavity. Devices and methods of the present invention utilize in preferred embodiments the advantageous features of a dual lumen catheter, preferably a T-fluted dual lumen catheter, combined with a substantially constant rate of dialysate inflow and a pressure-dependent outflow controller, also referred to herein as a "pressure regulator" or a "pressure-activated valve". The invention, therefore, provides in certain aspects advantageous systems for passing fluid through a patient's peritoneal cavity at a relatively high flow rate, while maintaining in the peritoneal cavity an optimal dialysate pressure, to thereby alter the contents of the patient's blood by diffusion of molecules through the peritoneal membrane.

In one aspect of the invention, there is provided a device for performing continuous flow peritoneal dialysis, comprising a dialysate source; a peritoneal fluid receptacle; a flexible catheter having a first segment comprising a conduit which defines a first lumen and a second lumen, and a second segment comprising a first limb which defines a recess in fluid communication with the first lumen and a second limb which comprises a T-fluted configuration defining recesses in fluid communication with the second lumen, the first and second limbs being formed to move independently of one another and having distal ends opposite the first segment; a first tube in fluid communication with the dialysate source and the first lumen; a second tube in fluid communication with the second lumen and the peritoneal fluid receptacle; and a pressure regulator in fluid communication with the second tube for maintaining a pressure within the peritoneal cavity of from about 6 to about 20.

In another aspect of the invention, there is provided a device for performing continuous flow peritoneal dialysis, comprising a dialysate source; peritoneal fluid receptacle; a first catheter in fluid communication with the dialysate source, the first catheter defining a first lumen and comprising a first segment configured to be positioned across a patient's abdominal wall and a second segment configured to reside in the patient's peritoneal cavity; a second catheter in fluid communication with the peritoneal fluid receptacle, the second catheter defining a second lumen and comprising a first segment configured to be positioned across a patient's abdominal wall and a second segment configured to reside in the patient's peritoneal cavity; a first tube in fluid communication with and positioned between the dialysate source and the first lumen; a second tube in fluid communication with and positioned between the second lumen and the peritoneal fluid receptacle; and a pressure regulator in fluid communication with the second tube for maintaining a pressure within the peritoneal cavity of from about 6 to about 20 mm Hg.

In accordance with another aspect of the invention, there is provided a method for removing toxins from a patient's blood, comprising passing a dialysate into a patient's peritoneal cavity through a first lumen of a flexible dual lumen catheter at a substantially continuous rate of from about 20 to about 300 ml/min; and recovering peritoneal fluid from the peritoneal cavity through a second lumen of the catheter, provided that fluid is recovered only when fluid in the peritoneal cavity reaches a pressure of from about 6 to about 20 mm Hg; wherein the catheter has a first segment comprising a conduit which defines a first lumen and a second lumen, and a second segment comprising a first limb which defines one or more recesses in fluid communication with the first lumen and a second limb which defines one or more recesses in fluid communication with the second lumen, the first and second limbs being formed to move independently of one another and having distal ends opposite the first segment.

In accordance with another aspect of the invention, there is provided a method for removing toxins from a patient's blood, comprising passing a dialysate into a patient's peritoneal cavity through a first lumen of a first catheter at a substantially continuous rate of from about 20 to about 300 ml/min; and recovering peritoneal fluid from the peritoneal cavity through a second lumen of a second catheter, provided that fluid is recovered only when fluid in the peritoneal cavity reaches a pressure of from about 6 to about 20 mm Hg; wherein the first and second catheters are positioned across the patient's abdominal wall, thereby providing access to the peritoneal cavity.

In accordance with another aspect of the invention, there is provided a device for performing continuous flow peritoneal dialysis, comprising a fluid container; a flexible catheter having a first segment comprising a conduit which defines a first lumen and a second lumen, and a second segment comprising a first limb which defines a recess in fluid communication with the first lumen and a second limb which comprises a T-fluted configuration defining recesses in fluid communication with the second lumen, the first and second limbs being formed to move independently of one another and having distal ends opposite the first segment; a first tube in fluid communication with the first lumen and in fluid communication with the fluid container; a second tube in fluid communication with the second lumen and in fluid communication with the fluid container; wherein the catheter is configured such that the second segment may be positioned within the peritoneal cavity of a patient such that the distal end of the first limb may be placed anterior to the patient's liver and the distal end of the second limb may be placed substantially adjacent the patient's pelvis, thereby forming a closed fluid circuit for passing dialysate through the peritoneal cavity in a substantially unidirectional manner.

In accordance with another aspect of the invention, there is provided a device for performing continuous flow peritoneal dialysis, comprising a fluid container; a first catheter in fluid communication with the fluid container, the first catheter defining a first lumen and comprising a first segment configured to be positioned across a patient's abdominal wall and a second segment configured to reside in the patient's peritoneal cavity; a second catheter in fluid communication with the fluid container, the second catheter defining a second lumen and comprising a first segment configured to be positioned across a patient's abdominal wall and a second segment configured to reside in the patient's peritoneal cavity; a first tube in fluid communication with and positioned between the container and the first lumen; a second tube in fluid communication with and positioned between the second lumen and the container; and a pressure regulator in fluid communication with the second tube for maintaining a pressure within the peritoneal cavity of from about 6 to about 20 mm Hg.

In accordance with another aspect of the invention, there is provided a method for removing toxins from a patient's blood, comprising passing a dialysate into a patient's peritoneal cavity from a fluid container through a first tube and a first lumen of a flexible dual lumen catheter at a substantially continuous rate of from about 20 to about 300 ml/min; and recovering peritoneal fluid from the peritoneal cavity through a second lumen of the catheter, provided that fluid is recovered only when fluid in the peritoneal cavity reaches a pressure of from about 6 to about 20 mm Hg; and passing the peritoneal fluid to the container through a second tube; wherein the catheter has a first segment comprising a conduit which defines a first lumen and a second lumen, and a second segment comprising a first limb which defines one or more recesses in fluid communication with the first lumen and a second limb which defines one or more recesses in fluid communication with the second lumen, the first and second limbs being formed to move independently of one another and having distal ends opposite the first segment.

In accordance with another aspect of the invention, there is provided a device for treating a patient for hepatic insufficiency, comprising a fluid container; a first conduit having a proximal end in fluid communication with the container for passing fluid from the container into a patient's peritoneal cavity through a distal end of the conduit; a second conduit having a proximal end in fluid communication with the container and a distal end in fluid communication with the peritoneal cavity for moving fluid from the peritoneal cavity to the container; and a bioreactor in fluid communication with the second conduit for conditioning the fluid.

In accordance with another aspect of the invention, there is provided a device for treating a patient for hepatic insufficiency, comprising a fluid container; a first conduit in fluid communication with the container; a second conduit in fluid communication with the container; a catheter having a proximal end, a first lumen and a second lumen, wherein the proximal end of the first lumen is in fluid communication with the first conduit, wherein the proximal end of the second lumen is in fluid communication with the second conduit, and wherein the first and second lumens have distal ends positioned in a patient's peritoneal cavity such that the first and second lumens are in fluid communication with the peritoneum, thereby providing a closed fluid circuit; means for passing fluid from the container, through the first conduit and first lumen and into the peritoneal cavity; and a bioreactor in fluid communication with the second conduit for conditioning fluid exiting the peritoneal cavity.

In accordance with another aspect of the invention, there is provided a method for treating a patient for hepatic insufficiency, comprising passing a fluid from a fluid container into a patient's peritoneal cavity at a rate of from about 20 to about 300 ml/min, the fluid selected from the group consisting of fresh dialysate, conditioned peritoneal fluid and mixtures thereof; removing peritoneal fluid from the peritoneal cavity at a rate which maintains a fluid pressure in the peritoneum of from about 6 to about 20 mm Hg; conditioning the peritoneal fluid by contacting the fluid with hepatocytes to provide a conditioned peritoneal fluid; and introducing the conditioned peritoneal fluid into the container.

In accordance with another aspect of the invention, there is provided a method for treating a patient for hepatic insufficiency, comprising providing a device comprising a fluid container, a first conduit having a proximal end in fluid communication with the container for passing fluid from the container into a patient's peritoneal cavity through a distal end of the conduit, a second conduit having a proximal end in fluid communication with the container for moving fluid from the peritoneal cavity to the container and a bioreactor in fluid communication with the second conduit for conditioning the fluid; placing a distal end of the first conduit and a distal end of the second conduit into the peritoneal cavity, thereby providing a closed fluid circuit; and passing fluid through the circuit, maintaining a fluid pressure within the peritoneal cavity of from about 6 to about 20 mm Hg.

It is an object of the present invention to provide improved methods of performing peritoneal dialysis for treating patients suffering from renal and/or hepatic insufficiency.

Further objects, advantages and features of the present invention will be apparent from the detailed description herein.

BRIEF DESCRIPTION OF THE FIGURES

Although the characteristic features of this invention will be particularly pointed out in the claims, the invention itself, and the manner in which it may be made and used, may be better understood by referring to the following description taken in connection with the accompanying figures forming a part hereof.

DESCRIPTION OF THE PREFERRED EMBODIMENTS

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention as described herein being contemplated as would normally occur to one skilled in the art to which the invention pertains.

The present invention relates generally to advantageous devices and methods for treating patients suffering from renal insufficiency and/or hepatic insufficiency. More particularly, the invention relates in certain aspects to devices and methods for performing continuous flow-through peritoneal dialysis (CFPD). In another aspect of the invention, a peritoneal dialysis system is provided which utilizes a bioreactor to regenerate peritoneal fluid for re-infusion into a peritoneal cavity. Devices and methods of the present invention utilize in preferred embodiments the advantageous features of a dual lumen catheter, preferably a T-fluted dual lumen catheter, combined with a substantially constant rate of dialysate inflow and a pressure-dependent outflow controller, also referred to herein as a "pressure regulator" or a "pressure-activated valve". The invention, therefore, provides in certain aspects advantageous systems for passing fluid through a patient's peritoneal cavity at a relatively high flow rate, while maintaining in the peritoneal cavity an optimal dialysate pressure, to thereby alter the contents of the patient's blood by diffusion of molecules through the peritoneal membrane.

Figure 1:
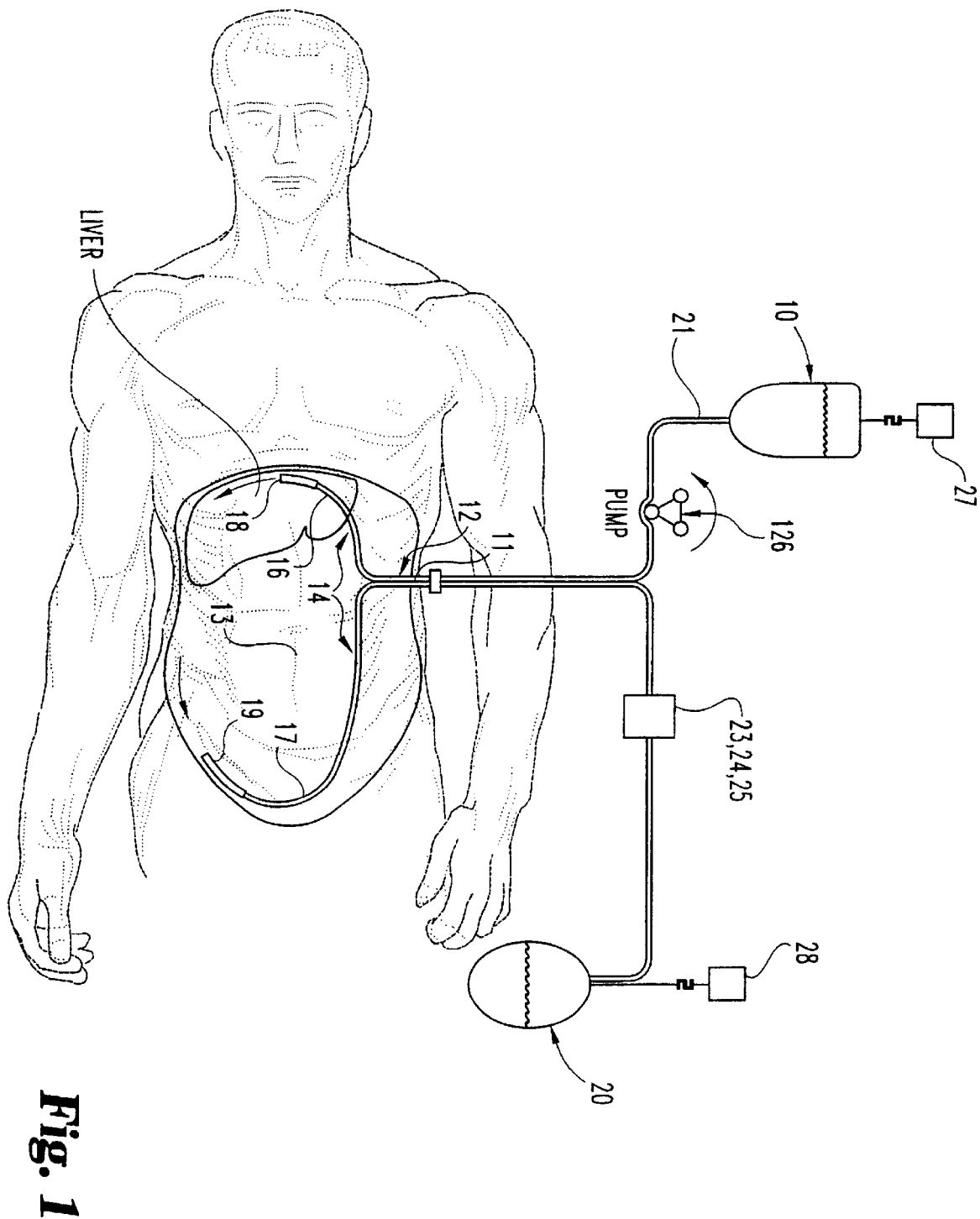
FIG. 1 is a schematic diagram showing a continuous flow-through peritoneal dialysis device in accordance with one preferred aspect of the invention in which a dual lumen catheter is used to access the patient's peritoneal cavity and in which a roller pump is used to maintain flow of dialysate into the peritoneal cavity.

In one aspect of the invention, a device for performing CFPD is provided this device being depicted schematically in FIG. 1. In this device 1, a dialysate source 10 is placed in fluid communication with a first lumen of a catheter 12 having at least two lumens. The dialysate source 10 may be, for example, a bag of pre-mixed dialysate, or may alternatively comprise a proportioning system for mixing sterile water (made by filtration from tap water) with a sterile dialysate concentrate. After being proportioned, the resulting fluid may be directly infused to the peritoneal cavity 13 at the same rate as it is created.

Figure 2:
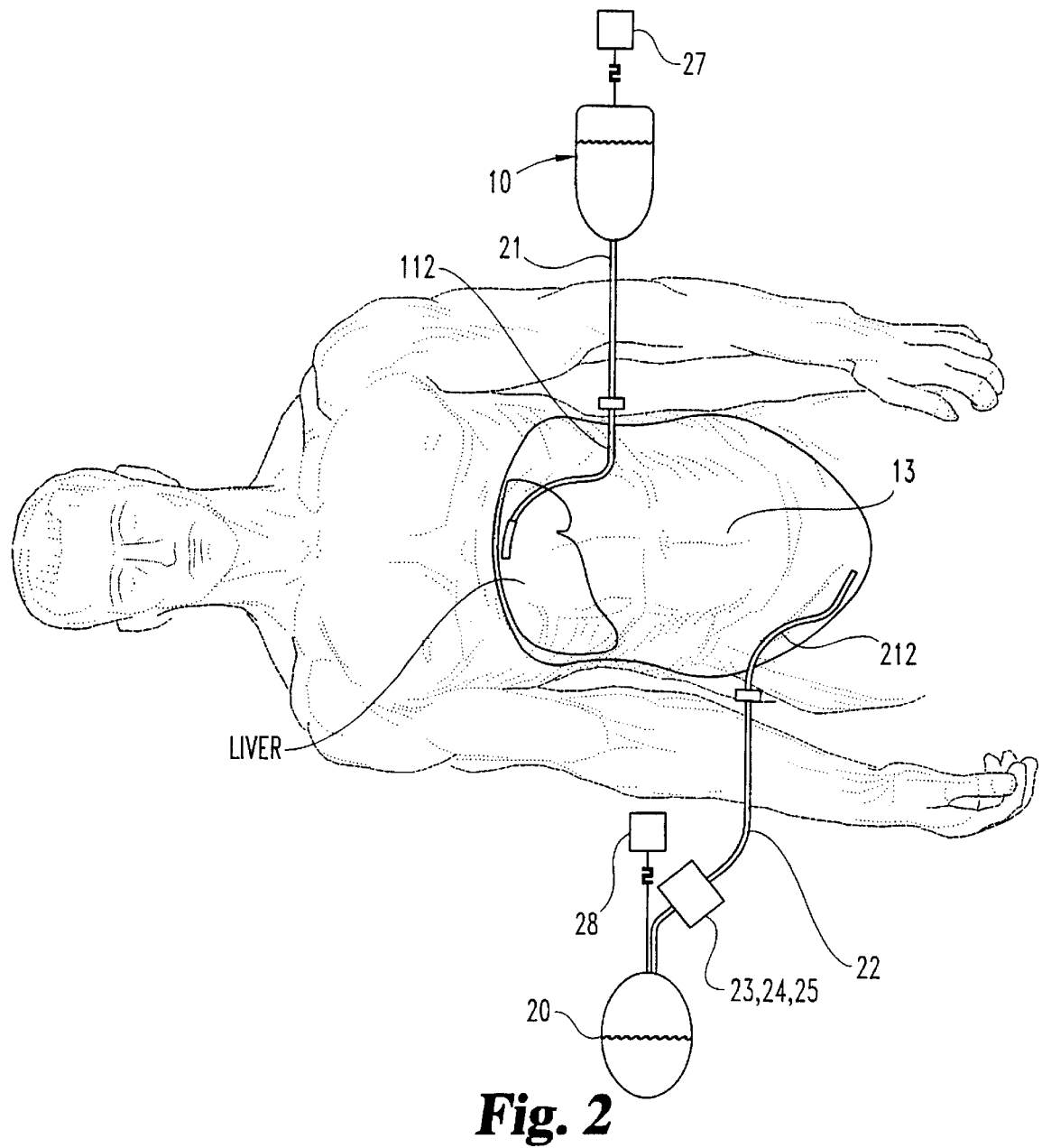
FIG. 2 is a schematic diagram showing a continuous flow-through peritoneal dialysis device in accordance with another preferred aspect of the invention in which two catheters are utilized, the catheters accessing the peritoneal cavity at two different locations, and in which gravity is utilized to achieve inflow of dialysate into the peritoneal cavity.
Figure 3:
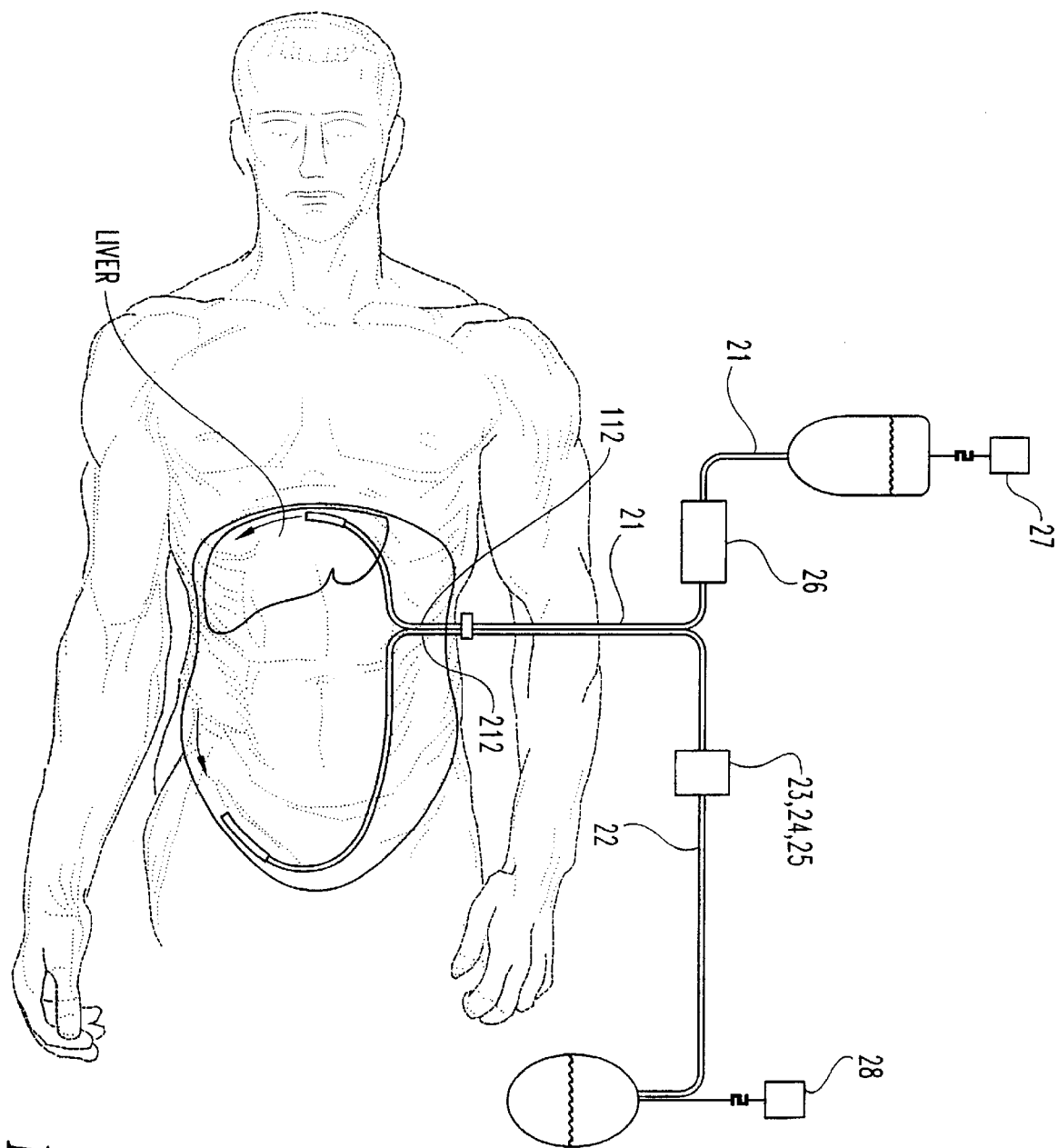
FIG. 3 is a schematic diagram wherein two catheters are utilized and wherein the catheters access the peritoneal cavity at the same locus.
Figure 4:
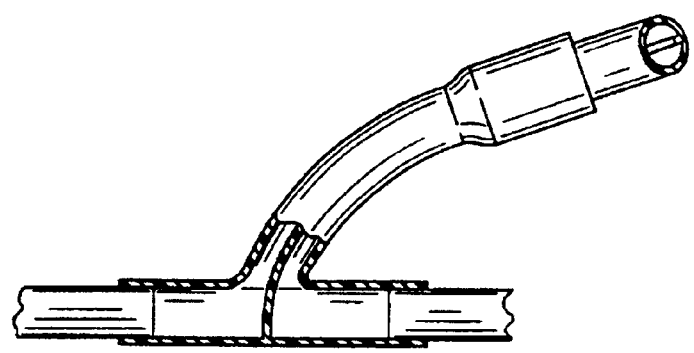
FIG. 4 is a partial cross-section of a dual lumen catheter suitable for use in accordance with the invention.

The catheter 12 is preferably formed such that it may be positioned across a patient's abdominal wall to provide access to the peritoneal cavity 13 for supplying dialysate thereto during peritoneal dialysis procedures. The distal segment (the "second segment" 14 of the catheter, i.e., the portion of the catheter configured to be placed within the peritoneal cavity 13), preferably comprises two limbs 16, 17, each limb defining therein a lumen for passing fluid into or out of the peritoneal cavity and capable of moving independently of one another. A suitable construction of a catheter which may be used in accordance with the invention is set forth in a partial sectional view in FIG. 4. Thus, the distal end 18 of the first limb 16 is preferably separately positionable from the distal end 19 of the second limb 17. It is to be understood that the present invention may alternatively utilize two catheters 112, 212, one for introducing dialysate into the peritoneal cavity 13 and a second for recovering peritoneal fluid from the cavity 13. Additionally, the two catheters 112, 212 in such an embodiment may provide access to the peritoneal cavity at two distinct loci (FIG. 2). However, it is preferred in accordance with the invention that the catheters 112, 212 access the peritoneal cavity 13 at a single locus to minimize trauma to the patient and the risk of infection (FIG. 3). More preferably, a single catheter 12 having at least two lumens, as set forth in FIG. 1 is used.

Figure 5:
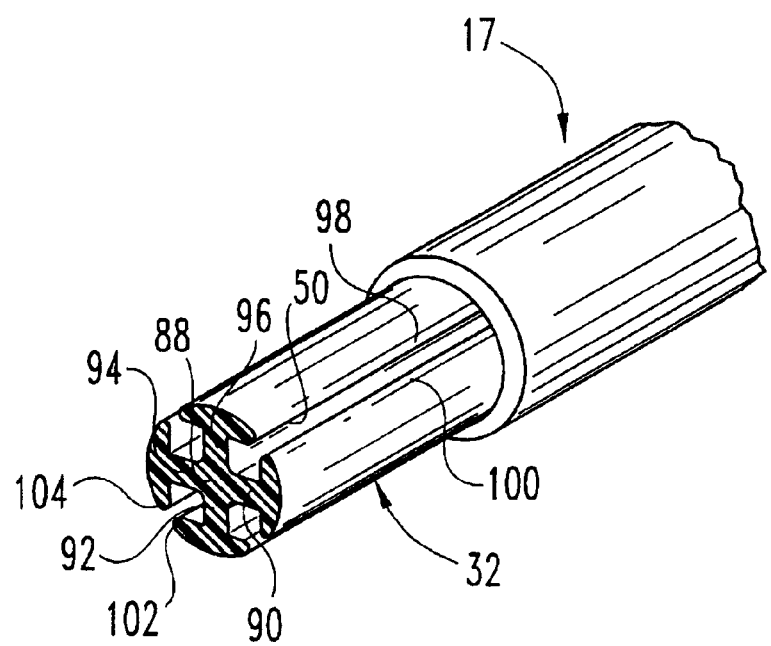
FIG. 5 is an elevational view of a liquid transport device which is advantageously positioned at the distal end of an outflow catheter or outflow limb of a dual lumen catheter for recovering fluid from the peritoneal cavity.

According to a preferred aspect of the invention, a dual lumen catheter 12 is used which is configured such that, in the first segment 15, i.e., the portion passing the abdominal wall, a single conduit defines the first and second lumens, thereby maintaining the first and second lumens substantially adjacent one another. In contrast, it is preferred that the second segment 14, i.e., the portion configured to reside within the peritoneal cavity 13, comprise two separate conduits, or limbs 16, 17 defining recesses in fluid communication with the first and second lumens (i.e., extensions of the first and second lumens). Therefore, the catheter 12 preferably has a first segment 15 comprising a conduit which defines a first lumen and a second lumen, and a second segment 14 comprising a first limb 16 which defines a recess in fluid communication with the first lumen and a second limb 17 which preferably comprises a T-fluted configuration defining recesses in fluid communication with the second lumen. The first and second limbs 16, 17 are preferably configured to move independently of one another and having distal ends 18, 19 opposite the first segment 15. As used herein and depicted in FIG. 5, the term "T-fluted" is intended to refer to liquid transport device 32 having a substantially cylindrical or ovoid configuration and a circular cross-sectional contour normal to its longitudinal axis. In the embodiment shown in FIG. 5, one or more longitudinal liquid transport recesses 50 are defined within by a core portion 88 with peripherally spaced struts 90, 92, 94 and 96 extending radially outwardly from the core portion 88. At the outer ends thereof, the struts terminate in overhang portions 98, 100, 102 and 104 that are coextensive in length with the struts. It is intended, however, that alternate designs fall within the scope of the invention. Preferred designs include means for preventing structures adjacent the liquid transport device 32, such as, for example, organs in the peritoneal cavity, from blocking flow of fluid into and through a longitudinal liquid transport recess 50. A wide variety of designs may be employed which advantageously provide for sufficient flow of fluid from the peritoneal cavity and through the second lumen.

Referring again to FIGS. 1–3, the device also comprises a peritoneal fluid receptacle 20 in fluid communication with the second lumen. When in use, therefore, the second lumen contains peritoneal fluid passing from the peritoneal cavity 13 to the peritoneal fluid receptacle 20. It is to be understood that the first and second lumens of the catheter or catheters may preferably be connected to the dialysate source 10 and the peritoneal fluid receptacle 20, respectively, using tubing. As used herein, a tube connecting the dialysate source and the first lumen is referred to as the first tube 21, and the tube connecting the peritoneal fluid receptacle and the second lumen is referred to as the second tube 22. Appropriate tubing may be readily selected by a person of ordinary skill in the art, and the first and second tubes preferably each have a length of from about 10 to about 30 centimeters.

For purposes of clarity, the term "dialysate" is used herein to refer to fluid being introduced into the peritoneal cavity through the first lumen, and the term "peritoneal fluid" is used to refer to fluid exiting the peritoneal cavity through the second lumen. It is understood that dialysate and peritoneal fluid are inherently the same fluid, i.e., are in contained within the same fluid pathway, and also that the compositional difference between dialysate and peritoneal fluid is dictated by the degree of diffusion of materials from the patient's blood, through the peritoneal membrane and into the dialysate as well as the degree of diffusion of materials from the dialysate, through the peritoneal membrane and into the patient's blood.

In accordance with the invention, the second tube 22, i.e., the tube in fluid communication with the second lumen at its distal end and the peritoneal fluid receptacle at its proximal end, preferably comprises means associated therewith for controlling the fluid pressure in the peritoneal cavity. The fluid pressure may be controlled in accordance with the invention using the force of gravity, such as, for example, by placing the peritoneal fluid receptacle at a level just above the peritoneum. Alternatively, it may be advantageously controlled using a pressure regulator 23, such as, for example, a stand-pipe drain or a valve with a defined opening pressure. In a particularly preferred embodiment, the pressure regulator 23 comprises a valve formed to pass fluid therethrough only when the fluid has a pressure at least as great as a predetermined threshold pressure. In one preferred aspect of the invention, the valve is a duck bill pressure valve in which a tapered, flexible structure with a central opening allows unidirectional flow when pressure exceeds a small, preset value. The valve selected in accordance with the invention preferably has an opening setting of from about 6 to about 20 mm Hg, more preferably, from about 8 to about 14 mm Hg and most preferably of about 12 mm Hg.

Also in accordance with the invention, the first tube 21 preferably comprises means associated therewith for maintaining a substantially continuous fluid flow rate in the first tube and the first lumen for passing dialysate into the peritoneal cavity. In a preferred embodiment, the flow rate maintaining means 26 comprises a pump formed to pass fluid therethrough at a predetermined rate. While a wide variety of pumps may be suitably used in accordance with the invention, in one preferred aspect of the invention, the pump is a roller pump 126. The pump selected in accordance with the invention is preferably capable of maintaining a flow rate of from about 20 to about 300 ml/min, more preferably, from about 70 to about 200 ml/min and most preferably of about 100 ml/min. It is understood that advantages may be had in accordance with the invention by using a pump having an adjustable flow rate. It is also understood that, in certain embodiments of the invention, no pump is used and inflow of dialysate into the peritoneal cavity is maintained using a gravity flow mechanism.

In a preferred manner of practicing the invention, a dual lumen catheter is positioned in a patient experiencing renal or hepatic insufficiency. A catheter suitable for use is the T-fluted dual lumen catheter disclosed in U.S. Pat. No. 5,322,519 to Ash, which patent is hereby incorporated herein by reference in its entirety. Preferably, the catheter 12 is positioned such that the distal end 18 of the first limb 16 of the catheter (i.e., the internal end of the "inflow" lumen) is placed substantially adjacent the liver in the anterior region of the patient's peritoneal cavity. It is understood by a person skilled in the art that a substantially permanent placement may be accomplished by positioning this limb between the abdominal wall and the falciform ligament where it would be restrained from movement. The distal end 19 of the second limb 17 of the catheter (i.e., the internal end of the "outflow" lumen) is preferably placed substantially adjacent the patient's pelvis in the posterior region of the peritoneal cavity. The second limb 17 is preferably held in place by apposition to the curved, closed surface of the peritoneum. The limbs 16, 17 of the catheter may be placed into appropriate positions using techniques known in the art including, for example, the use of endoscopic procedures.

Utilization of a dual lumen catheter 12 and directional flow of dialysate within the peritoneum advantageously diminishes the risk of infection in the peritoneal cavity by reducing the chance that the inflow lumen will become contaminated in single pass operation. This risk may be further reduced by placing a filter 24 in fluid communication with the first tube 21 to thereby remove potential contaminants from the dialysate before introducing the dialysate into the peritoneal cavity.

After positioning the catheter 12 (or catheters 112, 212) as described, the peritoneal dialysis device and the peritoneal cavity define a continuous fluid pathway for passing fluids from the dialysate source 10, through the first lumen, through the peritoneal cavity 13, through the second lumen and into the peritoneal fluid receptacle 20 in a continuous flow-through manner. A dialysate suitable for peritoneal dialysate, a wide variety of these being known, is provided in the dialysate source 10 and introduction of dialysate into the peritoneal cavity is begun at a continuous flow rate.

In one preferred aspect of the invention, continuous flow is provided using a roller pump 126 associated with the first tube 21. The roller pump 126 is preferably capable of adjustable speed control, and the inflow rate may thereby be controlled. In a preferred aspect of the invention, inflow of dialysate is maintained at a flow rate of from about 20 to about 300 ml/min, more preferably from about 70 to about 200 ml/min and most preferably at about 100 ml/min. Such a relatively high flow rate provides an advantageous level of toxin removal from the patient's blood. In this regard, urea clearances of up to about 30 ml/min may be achieved at a flow rate of about 100 ml/min, and creatinine clearances of up to about 20 ml/min may be achieved at a flow rate of about 100 ml/min.

Dialysate fluid therefore flows into the peritoneal cavity 13 at a substantially constant rate until the fluid pressure in the cavity reaches the threshold level for the pressure controller 23 integrally associated with the second tube 22. Preferably, the threshold level is from about 6 to about 20 mm Hg, more preferably from about 8 to about 14 mm Hg and most preferably at about 12 mm Hg. When the pressure in the cavity exceeds the threshold level, peritoneal fluid flows from the peritoneal cavity 13 through the second lumen, through the second tube 22 and the pressure controller 23, and into the peritoneal fluid receptacle 20.

In a preferred manner of practicing the invention, the rates of inflow and outflow are monitored to ensure that an excessive amount of fluid does not become present in the peritoneal cavity. Such an excessive amount may become present due to, for example, a kink in the outflow tube or a clog in the second lumen, pressure controller or second tube. In the event that any of these occur, it is critical that inflow be ceased so the patient does not experience excessive pressure in the peritoneal cavity, thereby over-distending the peritoneal membrane and potentially harming organs in the peritoneal cavity. Notification of such an occurrence may advantageously be accomplished in accordance with the invention by monitoring the weight of dialysate in the dialysate source 10 and the weight of peritoneal fluid in the peritoneal fluid receptacle 20. It is understood that, upon starting an inventive process, flow of dialysate from the dialysate source will cause an initial decrease in weight of the dialysate source without a corresponding increase in the weight of the peritoneal fluid receptacle. After approximately 2 liters of dialysate enter the peritoneal cavity of an average size adult (i.e., an amount sufficient to bring the fluid pressure in the peritoneal cavity to the desired level), the pressure controller 23 should open, thereby allowing peritoneal fluid to flow to the receptacle 20. From this point until the dialysis procedure is complete, the weight of the receptacle 20 should increase at a rate greater than the rate that the weight of the dialysate source 10 decreases. This phenomenon indicates that the outflow components of the device are functioning properly and that there is not excessive fluid pressure in the peritoneal cavity 13.

It is readily understood that the outflow rate should exceed the inflow rate because the fluid residing in the peritoneum increases volume as water follows the osmotic gradient to diffuse from the patient's blood into the fluid residing within the peritoneal cavity. During peritoneal dialysis treatments, the osmotic effect of glucose in the peritoneal fluid removes fluid from the patient by ultrafiltration, and ultrafiltrate increases the volume (and weight) of the dialysate. The amount of ultrafiltrate is adjusted by the concentration of glucose chosen for the dialysis procedure, as is known to a skilled artisan, so that the ultrafiltration equals the need for water and salt removal from the patient. For example, glucose concentrations commonly used range from about 1% to about 5% by weight. The weight of the dialysate source 10 and the peritoneal fluid receptacle 20 may preferably be determined using two simple hanging scales 27, 28. Additionally, the scales 27, 28 may preferably produce a signal which is electronically sent to a computer programmed to set off an alarm in the event that the outflow rate does not fall within the prescribed parameters.

Figure 6:
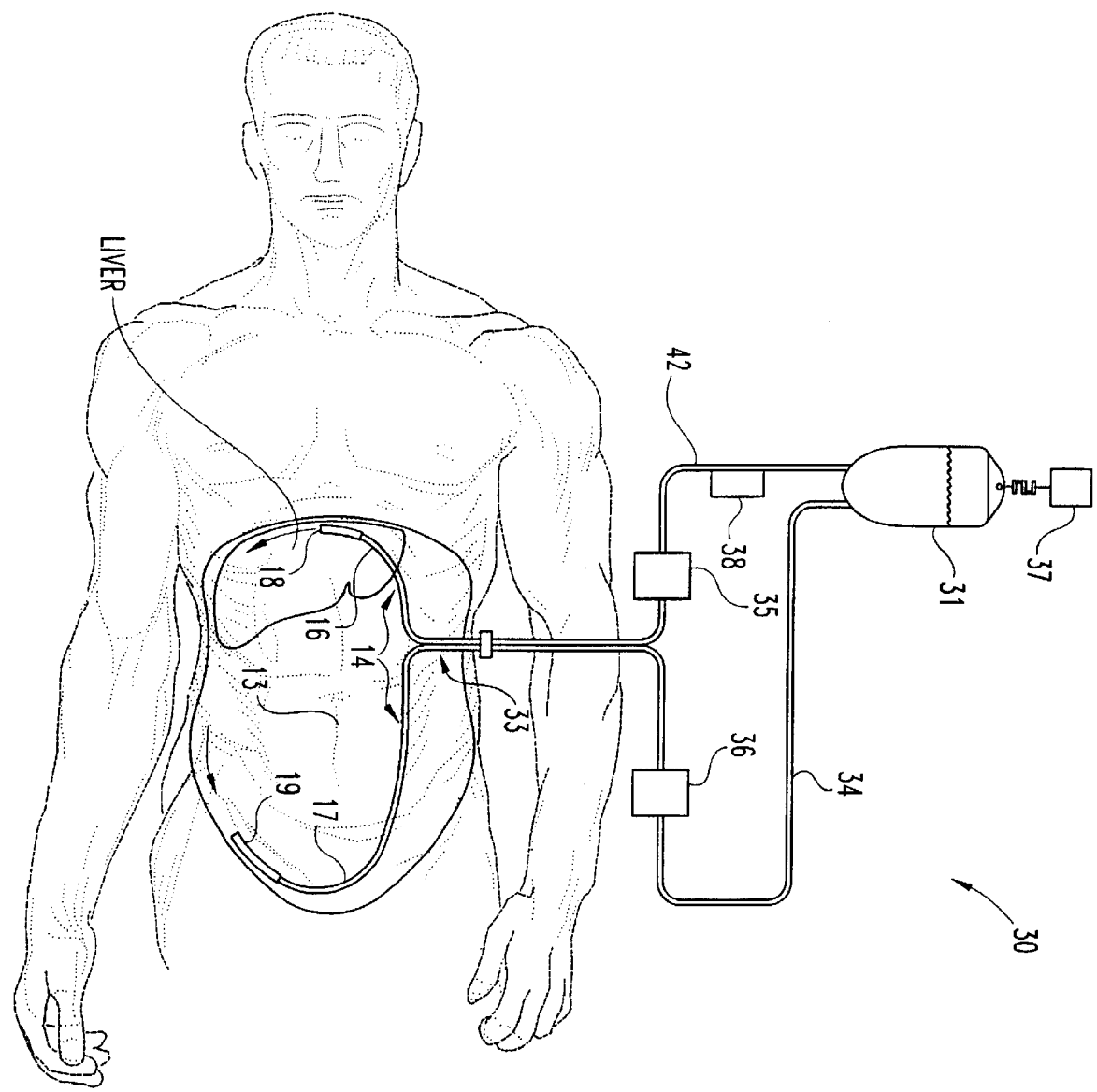
FIG. 6 is a schematic diagram showing a continuous flow-through peritoneal dialysis device in accordance with one preferred aspect of the invention in which a dual lumen catheter is used to access the patient's peritoneal cavity and which utilizes a single fluid container, thereby providing a continuous fluid circuit.
Figure 7:
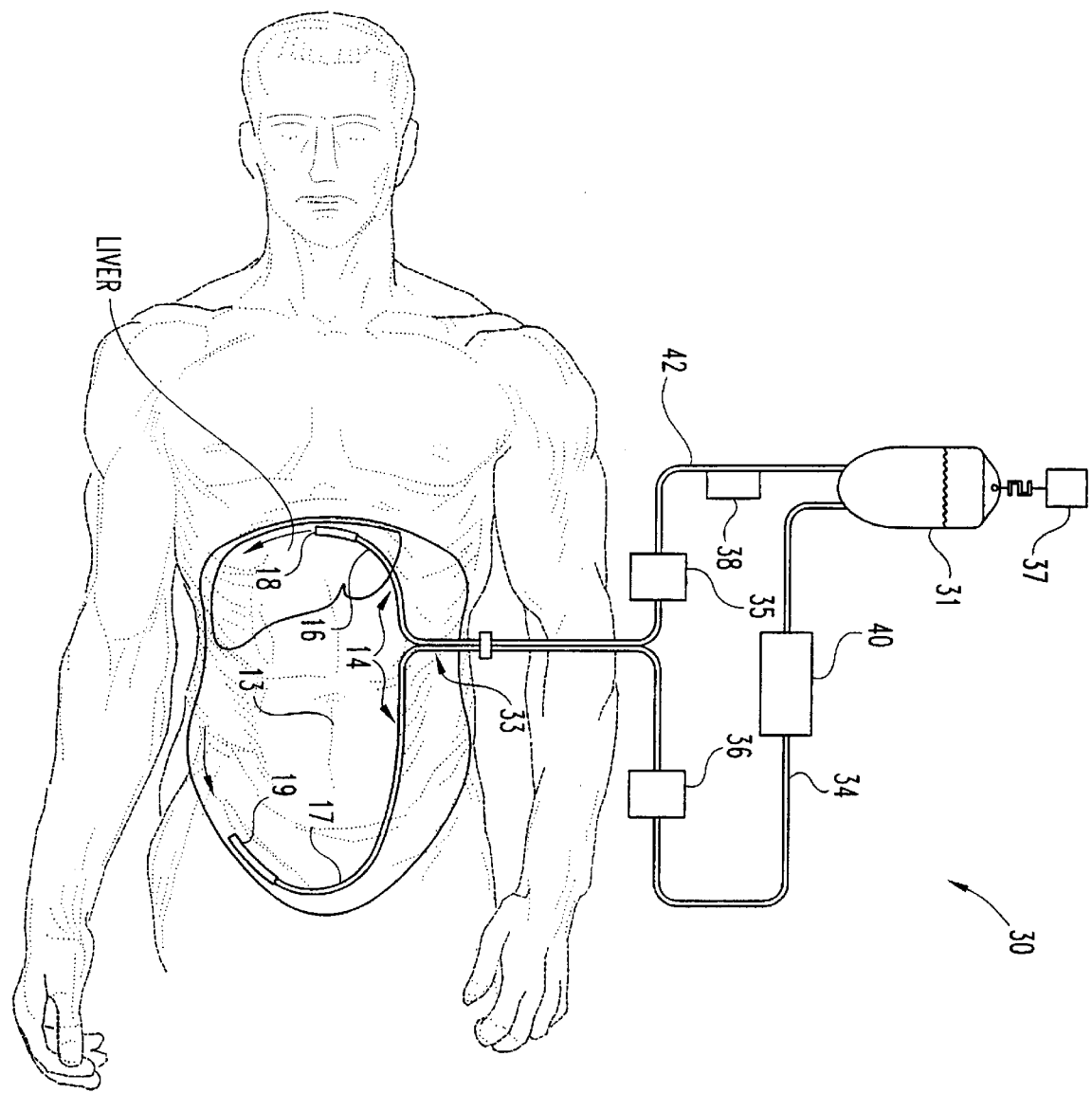
FIG. 7 is a schematic diagram as shown in FIG. 6, wherein a regenerating device is included in fluid communication with the second tube.
Figure 8:
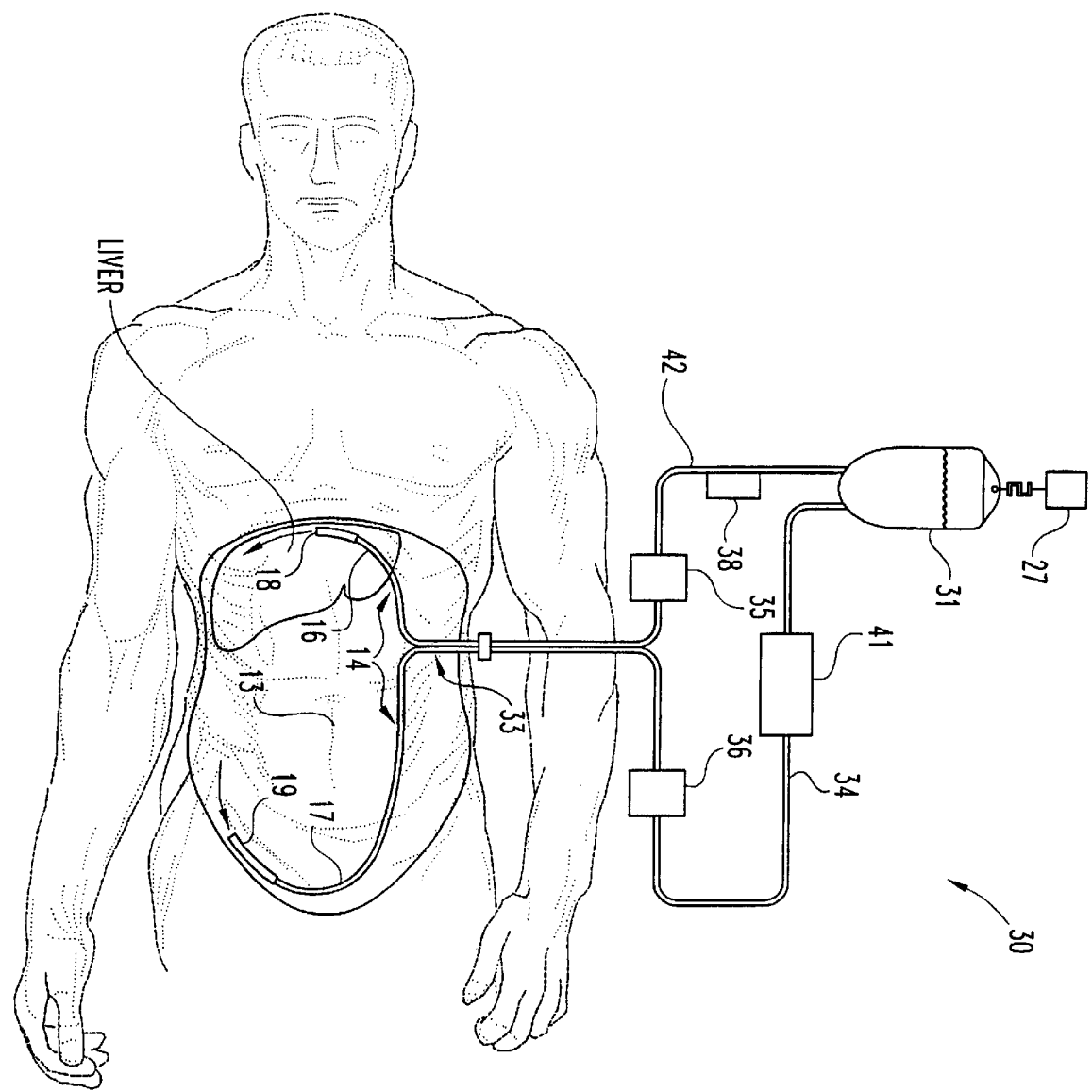
FIG. 8 is a schematic diagram as shown in FIG. 6, wherein a bioreactor is included in fluid communication with the second tube.

In an alternate aspect of the invention, a device 30 is provided for performing continuous flow through dialysis in a closed fluid circuit. In this aspect of the invention, there is a single fluid container 31 peritoneal fluid exiting the peritoneal cavity 13 is returned to the same container 31 from which it originated, and it is again passed through the peritoneal cavity 13 and returned to the container in a continuous cycle. Using such a device 30, as depicted schematically in FIG. 6, a relatively high flow rate of fluid, such as, for example, about 100 ml per minute, may be maintained while using a relatively small amount of dialysate during the treatment (compared to a single-pass treatment technique, in which large amounts of dialysate are required). This device comprises a first tube 21, a dual lumen catheter 12 (or multiple catheters 112, 212, using the same configuration as set forth in FIGS. 1–3) and a second tube 22; however, this device 30 comprises only one dialysate container 31 rather than a separate source and receptacle. Thus, there is provided a device 30 for performing peritoneal dialysis which uses a much smaller volume of dialysate, thereby providing the advantages attendant thereto. Also present in preferred embodiments of this device, providing the advantages described above, are a means 26 associated with the first tube 21 for maintaining a substantially constant flow rate and a pressure controller 23 in fluid communication with the second tube 22.

It is understood that, in this aspect of the invention, over-distention of the peritoneal cavity can be prevented by monitoring the weight of the single dialysate container 31. In the present system, a single scale 37, for example, having a capacity of about 25 kilograms, can be used to measure the amount of fluid in the fluid container. This scale 37 is preferably linked to appropriate computer hardware and software such that it can determine the amount of fluid which initially transfers into the patient (before outflow begins), the rate of ultrafiltration of fluid from the patient during treatment, and the amount of fluid drained from the abdomen at the end of the treatment. This single-scale measurement greatly simplifies the design of a cycler device for this therapy, eliminating the need for a separate scale for a dialysate source and a peritoneal fluid receptacle.

In this system, upon beginning flow of dialysate into the peritoneal cavity 13, the weight of the container 31 will initially decrease by an amount corresponding to the amount of fluid needed to achieve the desired fluid pressure in the peritoneal cavity 13. After this initial period of weight reduction, and as peritoneal fluid begins flowing into the container 31 from the second tube 22, the weight of fluid in the container should gradually increase as water moves by ultrafiltration from the patient's blood into the peritoneal fluid, thereby increasing the volume and, therefore, the weight of fluid in the system. As before, a scale 37 utilized to weigh the container preferably provides a signal to a computer program and, if the weight of the container 31 falls below a prescribed level, the program preferably sounds an alarm so that the fluid pathways can be examined for a kink, clog, leak or the like. Introduction of an excessive amount of fluid into the peritoneal cavity may therefore be avoided. Similarly, if the weight of the container 31 ceases to gradually increase, this indicates that there may be a problem with dialysate flow, thereby having caused ultrafiltration to cease.

To practice a preferred aspect of the invention, up to 20 liters of dialysate is placed in a fluid container 31, which is hung on a single scale 37 at the start of treatment. A roller pump 126 begins to operate, and infuses fluid from the container 31, through the first tube 21 and the first lumen. An in-line heater 38 may preferably be used to heat the fluid to body temperature as it passes through the first tube 21. The second limb 17 begins to drain peritoneal fluid after the peritoneal cavity 13 fills with sufficient fluid to bring fluid to this limb 17, and after the pressure on the outflow line exceeds the desired peritoneal pressure set on the outflow pressure control mechanism 23 (e.g., preferably about 10 mm Hg), the peritoneal fluid returns to the container 31 and mixes with the contents of the container 31 and eventually reinfuses to the patient.

In one preferred embodiment, the fluid entering the container 31 is directed so that it has minimal mixing with the fluid entering the patient. For example, the warmed peritoneal fluid could be directed to the top of the container 31, and the cooler dialysate removed from the bottom of the bag, so that density differences will minimize mixing between outflow and inflow fluid for the first 200 minutes of treatment. This will increase the clearance of toxins from the patient in the early portion of the treatment.

In a process as described above, there will be some loss of clearance as recirculation continues due to increasing toxin level in the fluid during treatment. The effect of re-use of dialysate on clearance can be readily predicted from the known clearance rates. The effect will only be a modest loss in clearance for small molecular substances (such as urea), and minimal loss of clearance for toxins of larger molecular weight (such as creatinine and phosphate). Clearance by CFPD, with 20 liters of fluid recirculated at 100 ml/min over 8 hours, could still equal or exceed that of CAPD therapies using 10–12 liters daily. In a preferred aspect of the invention, overall clearance of the system is improved by using a column of sorbents or a sorbent-based dialysis system to regenerate peritoneal fluid after leaving the abdomen and before re-entering the container. A sorbent regenerating system also minimizes the total fluid needed for initiating CFPD to approximately 2 liters.

Therefore, to improve the clearance of toxins from the patient's blood in one aspect of the invention, it is preferred that the fluid be conditioned before being reintroduced into the dialysate container. In a preferred manner of conditioning the peritoneal fluid, the fluid is passed through a regenerating device 40 using one of a wide variety of known techniques. Briefly, the peritoneal fluid may be passed along one side of a selectively permeable membrane while simultaneously passing a second dialysate fluid along the opposite side of the membrane, preferably in the opposite direction. In a preferred manner of dialyzing the peritoneal fluid, the second dialysate is in intimate contact with a sorbent column and/or a charcoal filter or is itself a sorbent suspension so that there remains a gradient across the dialyzer membrane for efficient removal of toxins across the membrane. For a more detailed description of a suitable regenerating device, reference is made to U.S. Pat. No. 5,277,820 to Ash, which is hereby incorporated by reference in its entirety and which may advantageously be used for regeneration of dialysate in accordance with the invention. It is understood that a membrane selected in accordance with the invention will preferably have a pore size suitable for removing small or medium size toxins. Therefore, the pore size is preferably from about 5,000 to about 50,000 Daltons.

While the above system may be advantageously utilized to improve the condition of a patient suffering from hepatic insufficiency, the overall effectiveness thereof with respect to liver failure patients is improved in accordance with an additional aspect of the invention, in which there is provided a CFPD system having excellent utility in the treatment of patients suffering from hepatic insufficiency. As set forth in the Background section above, attempts to devise an adequate treatment for hepatic insufficiency to provide a bridge until a liver transplant may be had, have to date proven largely unsuccessful. Hepatic failure is a condition in which the liver fails to maintain normal levels of toxins in the blood, and the patient develops illness leading to hypotension (low blood pressure), coma, respiratory failure, and, finally, kidney failure. Extracorporeal blood therapy with sorbent-based dialysis devices can remove many toxins which are dialyzable and bound to charcoal, and can slowly improve the mentation and physical status of the patient; however, such a device cannot remove toxins which are very strongly bound to large proteins (such as bilirubin, endotoxins and cytokines).

To address this problem, the present invention provides a manner for treating such a patient using a peritoneal dialysis method, preferably a CFPD device and method. During peritoneal dialysis, there is a removal of about 10–15 grams of large proteins each day, mostly albumin, but to a smaller extent, globulins. Also, ammonium, urea, manganese, creatinine, and numerous other smaller toxins of hepatic failure are removed.

In a peritoneal dialysis device for treating hepatic insufficiency made in accordance with the present invention, there is provided a bioreactor 41 in fluid communication with the outflow lumen. While it is believed that CFPD is the most advantageous peritoneal dialysis technique with which to utilize a bioreactor, it is expressly intended that the present invention also encompass the use of a bioreactor to treat outflowing peritoneal fluid of other peritoneal dialysis techniques, such as, for example, cycler techniques. The term "bioreactor" is used herein to refer to a device for contacting a fluid with live hepatocyte cells. Examples of suitable bioreactors for use in accordance with the invention are disclosed in U.S. Pat. No. 5,270,192 to Li et al. and that disclosed in U.S. Pat. No. 5,605,835 to Hu et al., which patents are incorporated herein by reference in their entirety. It is understood that the hepatocytes may be derived from a culture of human hepatocytes or may be hepatocytes from a non-human mammal such as, for example, porcine hepatocytes. In a system which utilizes a bioreactor, it is advantageous that the flow rate through the bioreactor be at least about 100 ml/min. In this way, sufficient oxygen is transferred to the hepatocytes by utilizing an oxygenator to transfer oxygen to the dialysate. Alternatively, hemoglobin complexes, red cells, or other oxygen carriers could be added to the dialysate without having much transfer to the patient due to slow permeation of the peritoneum. As there is only a minimal presence of immunoglobulins and white blood cells in the peritoneal fluid (in the absence of peritonitis) due to slow transfer across the peritoneum, hepatocyte function can be maintained for up to about 2 weeks where sufficient oxygen is available. In an alternate aspect of the invention, albumin is added to the dialysate to increase transfer of protein-bound toxins from the patient without having much transfer to the patient (due to slow permeation).

In a preferred manner of practicing this aspect of the invention, a predetermined amount of dialysate is provided, for example, about 2 to about 3 liters, in a fluid container. The dialysate is then passed into a patient's peritoneal cavity 13 through a first tube 21 and a first lumen of a double lumen catheter 12 at a predetermined rate. Preferably, the rate of inflow is from about 100 to about 400 ml/min, more preferably from about 200 to about 300. The fluid exits the peritoneal cavity 13, as described previously, after the fluid pressure in the cavity exceeds a threshold pressure, and the fluid then flows through the second lumen, the second tube 22 and the pressure controller 23. After passing through the pressure controller 23, the fluid enters a bioreactor 41 where it contacts hepatocytes. The hepatocytes advantageously metabolize protein-bound toxins in the peritoneal fluid, and also synthesize molecules which are then advantageously introduced into the peritoneal fluid. In this way, a continuous flow peritoneal dialysis procedure may be used to remove large, protein-bound toxins from the patient's blood, and also to introduce into the patient's blood molecules synthesized by the hepatocytes to overcome the insufficiency of the patient's native liver. The bioreactor 41 may advantageously used in combination with a regenerating device 40 to provide an advantageous system for regenerating peritoneal fluid. Therefore, there is preferably also for example, a sorbent system dialyzer in fluid communication with the second tube to further regenerate the peritoneal fluid. The system may advantageously utilize a simple column containing charcoal and cation exchangers.

For treatment of hepatic failure using the above-described device and method, treatment is preferably continued for 24 hours daily. At a flow rate of 100 ml/min, this passes 144 liters of fluid through the peritoneal cavity daily. In an alternate manner of practicing the invention, a flow rate of about 200 ml/min is utilized, in which case 288 liters of peritoneal fluid passes through the peritoneal cavity. In a preferred aspect of the invention, a 20 liter volume of dialysate is circulated through the above-described fluid circuit for about 8 hours, at which time it is replaced by a fresh 20 liter volume.

What is claimed is:

1. A device for performing continuous flow peritoneal dialysis, comprising:
    a dialysate source;
    a peritoneal fluid receptacle;
    a flexible catheter having a first segment comprising a conduit which defines a first lumen and a second lumen, and a second segment comprising a first limb which defines a recess in fluid communication with the first lumen and a second limb which defines a recess in fluid communication with the second lumen, the first and second limbs being formed to move independently of one another and having distal ends opposite the first segment;
    a first tube in fluid communication with the dialysate source and the first lumen;
    a second tube in fluid communication with the second lumen and the peritoneal fluid receptacle; and
    a pressure regulator in fluid communication with the second tube;
    wherein the pressure regulator is formed to prevent fluid flow therethrough when the fluid in the second tube has a pressure less than a predetermined threshold pressure and to pass fluid therethrough when the fluid in the second tube has a pressure at least as great as the predetermined threshold pressure; and
    wherein the predetermined threshold pressure is a pressure of from about 6 to about 20 mm Hg.

2. The device according to claim 1, further comprising a pumping device coupled to the first tube for moving the dialysate at a predetermined rate from the container to the peritoneal cavity through the first limb.

3. The device according to claim 1, further comprising a filter in fluid communication with the first tube such that fluid passing through the first tube passes through the filter.

4. The device according to claim 3, wherein the filter comprises a charcoal filter.

5. The device according to claim 1, further comprising a heater associated with the first tube such that fluid passing through the first lumen has a temperature of about 37° C.

6. The device according to claim 1, further comprising means for measuring the weight of the dialysate source; and means for measuring the weight of the peritoneal fluid receptacle.

7. The device in accordance with claim 1, wherein the second limb comprises a T-fluted configuration defining recesses in fluid communication with the second lumen.

8. A device for performing continuous flow peritoneal dialysis, comprising:
    a dialysate source;
    a peritoneal fluid receptacle;
    a first catheter in fluid communication with the dialysate source, the first catheter defining a first lumen and comprising a first segment configured to be positioned across a patient's abdominal wall and a second segment configured to reside in the patient's peritoneal cavity;
    a second catheter in fluid communication with the peritoneal fluid receptacle, the second catheter defining a second lumen and comprising a first segment configured to be positioned across a patient's abdominal wall and a second segment configured to reside in the patient's peritoneal cavity;
    a first tube in fluid communication with and positioned between the dialysate source and the first lumen;
    a second tube in fluid communication with and positioned between the second lumen and the peritoneal fluid receptacle; and
    a pressure regulator in fluid communication with the second tube;
    wherein the pressure regulator is formed to prevent fluid flow therethrough when the fluid in the second tube has a pressure less than a predetermined threshold pressure and to pass fluid therethrough when the fluid in the second tube has a pressure at least as great as the predetermined threshold pressure; and
    wherein the predetermined threshold pressure is a pressure of from about 6 to about 20 mm Hg.

9. The device according to claim 8, wherein the second segment of the second catheter comprises a T-fluted configuration defining recesses in fluid communication with the second lumen.

10. The device according to claim 8, wherein the second segment of the first catheter is configured to be positioned substantially adjacent the patient's liver such that inflowing dialysate enters the peritoneal cavity substantially adjacent the liver; and wherein the second segment of the second catheter is configured to be positioned substantially adjacent the patient's pelvis such that outflowing dialysate enters the second lumen substantially adjacent the pelvis.

11. A method for removing toxins from a patient's blood, comprising:

passing a dialysate into a patient's peritoneal cavity through a first lumen of a flexible dual lumen catheter at a substantially continuous rate of from about 20 to about 300 ml/min; and recovering peritoneal fluid from the peritoneal cavity through a second lumen of the catheter, provided that fluid is recovered only when fluid in the peritoneal cavity reaches a pressure of from about 6 to about 20 mm Hg;

wherein the catheter has a first segment comprising a conduit which defines a first lumen and a second lumen, and a second segment comprising a first limb which defines one or more recesses in fluid communication with the first lumen and a second limb which defines one or more recesses in fluid communication with the second lumen, the first and second limbs being formed to move independently of one another and having distal ends opposite the first segment;

wherein a pressure regulator in fluid communication with the second lumen remains closed when the fluid in the second lumen has a pressure less than a predetermined threshold pressure, thereby preventing fluid flow therethrough, and opens when the fluid in the second lumen has a pressure at least as great as the predetermined threshold pressure, thereby allowing fluid flow therethrough; and wherein the predetermined threshold pressure is a pressure of from about 6 to about 20 mm Hg.

12. The method according to claim 11, wherein the distal end of the first limb is placed substantially adjacent the patient's liver and the distal end of the second limb is placed substantially adjacent the patient's pelvis, thereby forming a closed fluid pathway for passing dialysate through the peritoneal cavity in a substantially unidirectional manner.

13. The method according to claim 11, wherein the second limb comprises a T-fluted configuration defining recesses in fluid communication with the second lumen.

14. The method according to claim 11, wherein the predetermined pressure is a pressure of from about 8 to about 14 mm Hg within the peritoneal cavity.

15. The method according to claim 11, wherein a filter is in fluid communication with the first lumen, the filter being placed between the dialysate source and the first lumen.

16. The method according to claim 8, wherein a pumping device is associated with the first lumen for moving dialysate at a predetermined rate through the first lumen.

17. A method for removing toxins from a patient's blood, comprising:

passing a dialysate into a patient's peritoneal cavity through a first lumen of a first catheter at a substantially continuous rate of from about 20 to about 300 ml/min; and recovering peritoneal fluid from the peritoneal cavity through a second lumen of a second catheter, provided that fluid is recovered only when fluid in the peritoneal cavity reaches a pressure of from about 6 to about 20 mm Hg;

wherein the first and second catheters are positioned across the patient's abdominal wall, thereby providing access to the peritoneal cavity;

wherein a pressure regulator in fluid communication with the second lumen remains closed when the fluid in the second lumen has a pressure less than a predetermined threshold pressure, thereby preventing fluid flow therethrough, and opens when the fluid in the second lumen has a pressure at least as great as the predetermined threshold pressure, thereby allowing fluid flow therethrough; and wherein the predetermined threshold pressure is a pressure of from about 6 to about 20 mm Hg.

18. A device for performing continuous flow peritoneal dialysis, comprising:

a fluid container;

a flexible catheter having a first segment comprising a conduit which defines a first lumen and a second lumen, and a second segment comprising a first limb which defines a recess in fluid communication with the first lumen and a second limb which defines a recess in fluid communication with the second lumen, the first and second limbs being formed to move independently of one another and having distal ends opposite the first segment;

a first tube in fluid communication with the first lumen and in fluid communication with the fluid container;

a second tube in fluid communication with the second lumen and in fluid communication with the fluid container; and a pressure regulator in fluid communication with the second tube;

wherein the pressure regulator is formed to prevent fluid flow therethrough when the fluid in the second tube has a pressure less than a predetermined threshold pressure and to pass fluid therethrough when the fluid in the second tube has a pressure at least as great as the predetermined threshold pressure;

wherein the predetermined threshold pressure is a pressure of from about 6 to about 20 mm Hg; and wherein the catheter is configured such that the second segment may be positioned within the peritoneal cavity of a patient such that the distal end of the first limb may be placed anterior to the patient's liver and the distal end of the second limb may be placed substantially adjacent the patient's pelvis, thereby forming a closed fluid circuit for passing dialysate through the peritoneal cavity in a substantially unidirectional manner.

19. The device according to claim 18, further comprising a bioreactor in fluid communication with the second conduit, the bioreactor containing hepatocytes.

20. The device according to claim 19, wherein said bioreactor comprises means for contacting the fluid with hepatocytes.

21. The device according to claim 18, further comprising a regenerating device in fluid communication with the second conduit.

22. The device according to claim 18, further comprising means for measuring the weight of the container.

23. The device in accordance with claim 18, wherein the second limb comprises a T-fluted configuration defining recesses in fluid communication with the second lumen.

24. A device for performing continuous flow peritoneal dialysis, comprising:

a fluid container;

a first catheter in fluid communication with the fluid container, the first catheter defining a first lumen and comprising a first segment configured to be positioned across a patient's abdominal wall and a second segment configured to reside in the patient's peritoneal cavity;

a second catheter in fluid communication with the fluid container, the second catheter defining a second lumen and comprising a first segment configured to be positioned across a patient's abdominal wall and a second segment configured to reside in the patient's peritoneal cavity;

a first tube in fluid communication with and positioned between the container and the first lumen;

a second tube in fluid communication with and positioned between the second lumen and the container; and a pressure regulator in fluid communication with the second tube;

wherein the pressure regulator is formed to prevent fluid flow therethrough when the fluid in the second tube has a pressure less than a predetermined threshold pressure and to pass fluid therethrough when the fluid in the second tube has a pressure at least as great as the predetermined threshold pressure; and wherein the predetermined threshold pressure is a pressure of from about 6 to about 20 mm Hg.

25. The device according to claim 24, wherein the second segment of the second catheter comprises a T-fluted configuration defining recesses in fluid communication with the second lumen.

26. The device according to claim 24, wherein the second segment of the first catheter is configured to be positioned substantially adjacent the patient's liver such that inflowing dialysate enters the peritoneal cavity substantially adjacent the liver; and wherein the second segment of the second catheter is configured to be positioned substantially adjacent the patient's pelvis such that outflowing dialysate enters the second lumen substantially adjacent the pelvis.

27. A method for removing toxins from a patient's blood, comprising:

passing a dialysate into a patient's peritoneal cavity from a fluid container through a first tube and a first lumen of a flexible dual lumen catheter at a substantially continuous rate of from about 20 to about 300 ml/min; and recovering peritoneal fluid from the peritoneal cavity through a second lumen of the catheter, provided that fluid is recovered only when fluid in the peritoneal cavity reaches a pressure of from about 6 to about 20 mm Hg; and passing the peritoneal fluid to the container through a second tube;

wherein the catheter has a first segment comprising a conduit which defines a first lumen and a second lumen, and a second segment comprising a first limb which defines one or more recesses in fluid communication with the first lumen and a second limb which defines one or more recesses in fluid communication with the second lumen, the first and second limbs being formed to move independently of one another and having distal ends opposite the first segment;

wherein a pressure regulator in fluid communication with the second lumen remains closed when the fluid in the second lumen has a pressure less than a predetermined threshold pressure, thereby preventing fluid flow therethrough, and opens when the fluid in the second lumen has a pressure at least as great as the predetermined threshold pressure, thereby allowing fluid flow therethrough; and wherein the predetermined threshold pressure is a pressure of from about 6 to about 20 mm Hg.

28. The method according to claim 27, wherein the distal end of the first limb is placed substantially adjacent the patient's liver and the distal end of the second limb is placed substantially adjacent the patient's pelvis, thereby forming a closed fluid circuit for passing dialysate through the peritoneal cavity in a substantially unidirectional manner.

29. The method according to claim 27, wherein the second limb comprises a T-fluted configuration defining recesses in fluid communication with the second lumen.

30. The method according to claim 27, wherein the predetermined threshold pressure is a pressure of from about 8 to about 14 mm Hg.

31. The method according to claim 27, further comprising conditioning the dialysate fluid before introducing the fluid into the container.

32. The method according to claim 31, wherein said conditioning comprises passing the fluid through a bioreactor containing hepatocytes.

33. The method according to claim 32, wherein the bioreactor comprises means for contacting the fluid with hepatocytes.

34. The method according to claim 31, wherein said conditioning comprises dialyzing the fluid.

35. A device for treating a patient for hepatic insufficiency, comprising:

a fluid container;

a first conduit having a proximal end in fluid communication with the container for passing fluid from the container into a patient's peritoneal cavity through a distal end of the conduit;

a second conduit having a proximal end in fluid communication with the container and a distal end in fluid communication with the peritoneal cavity for moving fluid from the peritoneal cavity to the container; and a bioreactor in fluid communication with the second conduit for conditioning the fluid;

wherein the bioreactor contains hepatocytes and is configured to contact the fluid with the hepatocytes.

36. A device for treating a patient for hepatic insufficiency, comprising:

a fluid container;

a first conduit in fluid communication with the container;

a second conduit in fluid communication with the container;

a catheter having a proximal end, a first lumen and a second lumen, wherein the proximal end of the first lumen is in fluid communication with the first conduit, wherein the proximal end of the second lumen is in fluid communication with the second conduit, and wherein the first and second lumens have distal ends positioned in a patient's peritoneal cavity such that the first and second lumens are in fluid communication with the peritoneum, thereby providing a closed fluid circuit;

means for passing fluid from the container, through the first conduit and first lumen and into the peritoneal cavity; and a bioreactor in fluid communication with the second conduit for conditioning fluid exiting the peritoneal cavity;

wherein the bioreactor contains hepatocytes and is configured to contact the fluid with the hepatocytes.

37. A method for treating a patient for hepatic insufficiency, comprising:

passing a fluid from a fluid container into a patient's peritoneal cavity at a rate of from about 20 to about 300 ml/min, the fluid selected from the group consisting of fresh dialysate, conditioned peritoneal fluid and mixtures thereof;

removing peritoneal fluid from the peritoneal cavity at a rate which maintains a fluid pressure in the peritoneum of from about 6 to about 20 mm Hg;

conditioning the peritoneal fluid by contacting the fluid with hepatocytes to provide a conditioned peritoneal fluid; and introducing the conditioned peritoneal fluid into the container.

38. A method for treating a patient for hepatic insufficiency, comprising:

providing a device comprising a fluid container, a first conduit having a proximal end in fluid communication with the container for passing fluid from the container into a patient's peritoneal cavity through a distal end of the conduit, a second conduit having a proximal end in fluid communication with the container for moving fluid from the peritoneal cavity to the container and a bioreactor in fluid communication with the second conduit for conditioning the fluid, wherein the bioreactor contains hepatocytes and is configured to contact the fluid with the hepatocytes;

placing a distal end of the first conduit and a distal end of the second conduit into the peritoneal cavity, thereby providing a closed fluid circuit; and passing fluid through the circuit, maintaining a fluid pressure within the peritoneal cavity of from about 6 to about 20 mm Hg.

39. A continuous flow peritoneal dialysis system comprising:

a source of peritoneal dialysis fluid;

an inflow line adapted for connection to a first lumen of a member selected from the group consisting of a double-lumen catheter implanted in the peritoneal cavity of a patient and a first single-lumen catheter implanted in the peritoneal cavity of a patient;

an outflow line adapted for connection to a second lumen of a member selected from the group consisting of the double-lumen catheter and a second single-lumen catheter implanted in the peritoneal cavity of a patient; and a pressure regulator in fluid communication with said outflow line for allowing flow through the outflow line only when a pressure is reached within the peritoneal cavity of from about 6 to about 20 mm Hg, the pressure regulator formed to prevent fluid flow therethrough when the fluid in the second tube has a pressure less than a predetermined threshold pressure and to pass fluid therethrough when the fluid in the second tube has a pressure at least as great as the predetermined threshold pressure;

wherein the predetermined threshold pressure is a pressure of from about 6 to about 20 mm Hg; and wherein infusion of a dialysate from said dialysate source through said inflow line and into the peritoneal cavity is controlled independent of flow rate in the outflow line.

40. A process for performing continuous flow peritoneal dialysis, comprising:

providing a dialysate flow circuit in fluid communication with a patient's peritoneal cavity, the circuit including a dialysate source, an inflow line, an outflow line and a pressure regulator in fluid communication with the outflow line, the pressure regulator being formed to prevent fluid flow therethrough when the fluid in the outflow line has a pressure less than a predetermined threshold pressure and to pass fluid therethrough when the fluid in the outflow line has a pressure at least as great as the predetermined threshold pressure;

passing dialysate into the patient's peritoneal cavity through the inflow line at a rate of from about 20 to about 300 ml/min; and recovering peritoneal fluid from the peritoneal cavity through the outflow line, provided that fluid is recovered only when fluid in the peritoneal cavity reaches the predetermined pressure.

41. The process in accordance with claim 40, wherein the rate that dialysate is passed into the patient's peritoneal cavity is controlled independent of flow rate in the outflow line.

* * * * *

UNITED STATES PATENT AND TRADEMARK OFFICE
CERTIFICATE OF CORRECTION

PATENT NO. : 6,409,699 B1
DATED : June 25, 2002
INVENTOR(S) : Stephen R. Ash

It is certified that error appears in the above-identified patent and that said Letters Patent is hereby corrected as shown below:

<u>Column 19,</u>
Line 49, please delete "8" and insert thereof -- 11 --.

Signed and Sealed this

Twenty-second Day of March, 2005

JON W. DUDAS
*Director of the United States Patent and Trademark Office*